US008722890B2

(12) United States Patent
Michaelides et al.

(10) Patent No.: US 8,722,890 B2
(45) Date of Patent: May 13, 2014

(54) THIENO[3,2-C]PYRIDINE KINASE INHIBITORS WITH IMPROVED CYP SAFETY PROFILE

(75) Inventors: Michael R. Michaelides, Libertyville, IL (US); Robin Frey, Libertyville, IL (US); Michael Curtin, Pleasant Prairie, WI (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/585,333

(22) Filed: Aug. 14, 2012

(65) Prior Publication Data

US 2012/0309783 A1 Dec. 6, 2012

Related U.S. Application Data

(63) Continuation of application No. 12/632,183, filed on Dec. 7, 2009, now abandoned.

(60) Provisional application No. 61/120,281, filed on Dec. 5, 2008, provisional application No. 61/223,760, filed on Jul. 8, 2009.

(51) Int. Cl.
C07D 495/04 (2006.01)
A61K 31/4365 (2006.01)

(52) U.S. Cl.
USPC .......................................... 546/114; 514/301

(58) Field of Classification Search
None
See application file for complete search history.

(56) References Cited

U.S. PATENT DOCUMENTS

| 3,470,183 | A | 9/1969 | Roth Barbara |
| 4,767,766 | A | 8/1988 | Baker et al. |
| 5,434,150 | A | 7/1995 | Austel et al. |
| 5,834,500 | A | 11/1998 | Wagner et al. |
| 6,500,855 | B1 | 12/2002 | Lam et al. |
| 7,202,363 | B2 | 4/2007 | Betschmann et al. |
| 7,592,352 | B2 | 9/2009 | Miyazaki |
| 7,737,160 | B2 | 6/2010 | Betschmann et al. |
| 2001/0044538 | A1 | 11/2001 | Cheng et al. |
| 2002/0004511 | A1 | 1/2002 | Luzzio et al. |
| 2002/0013354 | A1 | 1/2002 | Cheng et al. |
| 2002/0151544 | A1 | 10/2002 | Hayakawa et al. |
| 2005/0043347 | A1 | 2/2005 | Betschmann et al. |
| 2005/0143398 | A1 | 6/2005 | Das et al. |
| 2006/0069116 | A1 | 3/2006 | Ashton et al. |
| 2006/0100232 | A1 | 5/2006 | Summers et al. |
| 2007/0032512 | A1 | 2/2007 | Ji et al. |
| 2007/0093515 | A1 | 4/2007 | Arrington et al. |
| 2008/0021026 | A1 | 1/2008 | Kahraman et al. |
| 2010/0069371 | A1 | 3/2010 | Betschmann et al. |

FOREIGN PATENT DOCUMENTS

| EP | 39108 | A1 | 11/1981 |
| EP | 119828 | A2 | 9/1984 |
| EP | 0300688 | A1 | 1/1989 |
| EP | 0322852 | A1 | 7/1989 |
| EP | 0359354 | A1 | 3/1990 |
| EP | 0400947 | A1 | 12/1990 |
| EP | 438261 | A2 | 7/1991 |
| EP | 0630031 | A2 | 12/1994 |
| EP | 0754831 | A1 | 1/1997 |
| EP | 0756625 | A1 | 2/1997 |
| EP | 2071827 | A2 | 6/2009 |
| WO | WO 9713771 | A1 | 4/1997 |
| WO | WO 9847879 | A1 | 10/1998 |
| WO | WO 0039108 | A1 | 7/2000 |
| WO | WO 0119828 | A2 | 3/2001 |
| WO | WO 02071827 | A2 | 9/2002 |
| WO | WO 03000688 | A1 | 1/2003 |
| WO | WO 03022852 | A2 | 3/2003 |
| WO | WO 03059354 | A2 | 7/2003 |
| WO | WO 2004100947 | A2 | 11/2004 |
| WO | WO 2005010009 | A1 | 2/2005 |
| WO | WO 2006030031 | A1 | 3/2006 |
| WO | WO 2007054831 | A2 | 5/2007 |
| WO | WO 2007056625 | A2 | 5/2007 |
| WO | WO 2007067781 | A2 | 6/2007 |

OTHER PUBLICATIONS

Abdelraek F.M., et al., "Heterocyclic Synthesis with Nitriles: a new Approach to Thiophene and Tieno-[2,3-d]-Pyrimidine Derivates," Journal of prakt. Chemie. Band, 1988, vol. 330 (4), pp. 585-589.
Abdelraek F.M., et al., "Heterocyclic Synthesis with Nitriles: a Novel Synthesis of some Thiophene and Thieno[2,3-d]Pyrimidine Derivates, II [1]," Z. Naturforsch, 1989, vol. 44b, pp. 488-492.
Abdelraek F.M., et al., "Heterocyclic Synthesis with Nitriles: Synthesis of some new Thiophene and Thieno[2,3-d]Pyrimidine Derivates IV," Phosphorus, Sulfur, and Silicon, 1996, vol. 119, pp. 271-277.
Abdelraek F.M., et al., "Heterocyclic Synthesis with Nitriles: Synthesis of Some Novel Thiophene and Thieno[2,3-d]Pyrimidine Derivates," Phosphorus, Sulfur, and Silicon, 1992, vol. 71, pp. 93-97.
Abdelraek F.M., et al., "Synthesis of Novel Thieno[2,3-d]Pyrimidine, Thieno12,3- Bipyridine and Thiazolo[3,2-a]Pyrimidine Derivates and their effect on the Production of Mycotoxins," Arch Pharm, 1992, vol. 325, pp. 301-305.
Araki K., et al., "High Expression of Aurora-B/Aurora and IpII-like Midbody-associated Protein (AIM-1) in Astrocytomas ," Journal of Neuro-Oncology., 2004, vol. 67 (1-2), pp. 53-64.
Bischoff J.R., et al., "A Homologue of Drosophila Aurora Kinase is Oncogenic and Amplified in Human Colorectal Cancers," The EMBO Journal, 1998, vol. 17 (11), pp. 3052-3065.
Bodvarsdottir S.K., et al., "Aurora-A mplification Associated with BRCA2 Mutation in Breast Tumours," Cancer Letter, 2007, vol. 248 (1), pp. 96-102.
Chen J., et al., "Association between Aurora-A Kinase Polymorphisms and Age of Onset of Hereditary Nonpolyposis Colorectal Cancer in a Caucasian Population," Molecular Carcinogensis, 2007, vol. 46 (4), pp. 249-256.

(Continued)

Primary Examiner — David K O Dell
(74) Attorney, Agent, or Firm — Lisa V. Mueller; Michael Best & Friedrich LLP

(57) ABSTRACT

Compounds that inhibit protein kinases such as Aurora-kinases and the VEGFR and PDGFR families of kinases, with an improved safety profile due to low CYP3A4 inhibition, compositions containing the compounds and methods of treating diseases using the compounds are disclosed.

7 Claims, No Drawings

(56) References Cited

OTHER PUBLICATIONS

Chieffi P., et al., "Aurora B Expression Directly Correlates with Prostate Cancer Malignancy and Influence Prostate Cell Proliferation," Prostate, 2006, vol. 66 (3), pp. 326-333.

Comperat E., et al., "Aurora-A/STK-15 is a Predictive Factor for Recurrent Behaviour in Non-Invasive Bladder Carcinoma: A Study of 128 cases of Non-Invasive Neoplasms," Virchows Archiv, 2007, vol. 450 (4), pp. 419-424.

Co-pending U.S. Appl. No. 12/623,026, filed Nov. 20, 2009.

Cox D.G., et al., "Polymorphisms of the AURKA (STK15/Aurora Kinase) Gene and Breast Cancer Risk," Cancer Causes Control, 2006, vol. 17 (1), pp. 81-83.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Dave G., et al., "Gould-Jacob type of reaction in the synthesis of thieno[3,2-e]pyrimido{1,2-c pyrimidines: a comparison of classical heating vs solvent-free microwave irradiation," Heterocycles, 1999, vol. 51 (8), pp. 1819-1826.

Dimitrov S., et al., "Endothelial Apoptotic Activity of Angiocidin is Dependent on its Polyubiquitin Binding Activity," British Journal of Cancer, 2005, vol. 93 (6), pp. 662-669.

Ellis L.M., et al, "VEGF—Targeted Therapy Mechanisms of Anti-Tumour Activity," nature reviews cancer, 2008, vol. 8 (8), pp. 579-591.

Ewart T.A., et al., "Aurora-A/STK15 T+91A is a General Low Penetrance Cancer Susceptibility Gene: A Meta-Analysis of Multiple Cancer types," Carcinogenesis, 2005, vol. 26 (8), pp. 1368-1373.

Ewart-Toland A., et al., "Identification of Stk6/STK15 as a Candidate Low-Penetrance Tumor-Susceptibility Gene in Mouse and Human," Nature Genetics, 2003, vol. 34 (4), pp. 403-412.

Ferrera N., et al, "The Biology of VEGF and its Receptors," Nature Medicine, 2003, vol. 9 (6), pp. 669-676.

Fraizer G.C., et al., "Aurora-A/STK15/BTAK Enhances Chromosomal Instability in Bladder Cancer Cells," International Journal of Oncology, 2004, vol. 25 (6), pp. 1631-1639.

Gu J., et al., "Polymorphisms of STK15 (Aurora-A) Gene and Lung Cancer Risk in Caucasians," Carcinogenesis, 2007, vol. 28 (2), pp. 350-355.

Heyman H.R., et al, "Thienopyridine Urea Inhibitors of KDR Kinase," Bioorganic and Medicinal Chemistry Letters, 2007, vol. 17 (5), pp. 1246-1249.

Hienonen T., et al., "Preferential Amplification of AURKA 91A (Ile31) in Familial ColorectalCancers," International Journal of Cancer, 2006, vol. 118 (2), pp. 505-508.

Hoque A., et al., ""Loss of Aurora A/STK15/BTAK Overexpression Correlates with Transition of in Situ to Invasive Ductal Carcinoma of the Breast,""" Cancer Epidemiology, Biomarkers and Prevention, 2003, vol. 12 (2), pp. 1518-1522.

International Search Report and Written Opinion for Application No. PCT/US2009/066725, mailed on Jul. 14, 2010, 16 pages.

Jeng Y.M., et al., "Overexpression and Amplification of Aurora-A in Hepatocellular Carcinoma," Clinical Cancer Research, 2004, vol. 10 (6), pp. 2065-2071.

Ju H., et al., "Functional Polymorphism 57Val>Ile of Aurora Kinase A Associated with Increased Risk of Gastric Cancer Progression," Cancer Letter, 2006, vol. 242 (2), pp. 273-279.

Kandeel Z.E., et al., "Nitrites in Heterocyclic Synthesis: a Novel Synthesis of some Thieno[2,3- d]Pyrimidine and Thieno[2,3-b]Pyridine Derivates," Heteroatom Chemistry, 1996, vol. 7 (1), pp. 29-33.

Keen N., et al., "Aurora-Kinase Inhibitors as Anticancer Agents," Natuer Reviews Cancer, 2004, vol. 4 (12), pp. 927-936.

Kimura M.T., et al., "Two Functional Coding Single Nucleotide Polymorphisms in STK15 (Aurora-A) Coordinately Increase Esophageal Cancer Risk," Cancer Research, 2005, vol. 65 (9), pp. 3548-3554.

Klein A., et al., "Overexpression and Amplification of STK15 in Human Gliomas," International Journal of Oncology, 2004, vol. 25 (6), pp. 1789-1794.

Kolb A.J., et al., "Tyrosine Kinase Assays Adapted to Homogeneous Time-Resolved Fluorescence," Drug Discovery Today, 1998, vol. 3 (7), pp. 333-342.

Kurahashi T., et al., "Significance of Aurora-A expression in renal cell carcinoma," Urologic Oncology, 2007, vol. 25 (2), pp. 128-133.

Landen C.N., et al, ""Overexpression of the Centrosomal Protein Aurora-A Kinase is Associated with Poor Prognosis in Epithelial Ovarian Cancer Patients,"" Clinical Cancer Research, 2007, vol. 13 (14), pp. 4098-4104.

Lassmann S., et al., ""PredictiveValue of Aurora-A/STK15 Expression for Late Stage Epithelial Ovarian Cancer Patients Treated by Adjuvant Chemotherapy,"" Clinical Cancer Research, 2007, vol. 13 (14), pp. 4083-4091.

Li D., et al., ""Overexpression of Oncogenic STK15/BTAK/Aurora A Kinase in Human Pancreatic Cancer1,"" Clinical Cancer Research, 2003, vol. 9 (3), pp. 991-997.

Li F.C., et al., "[Deletion of P15 and P16 Genes and Overexpression of STK15 Gene in Human Laryngeal Squamous Cell Carcinoma].," National Medical Journal of China, 2003, vol. 83 (4), pp. 316-319.

Lin Y.S., et al, "Gene Expression Profiles of the Aurora Family Kinases," Gene Expression, 2006, vol. 13(1), pp. 15-26.

Lo Y.L., et al., "Breast Cancer Risk Associated with Genotypic Polymorphism of the Mitosis-Regulating Gene Aurora-A/STK15/BTAK," International Journal of Cancer, 2005, vol. 115 (2), pp. 276-283.

Mathis G., "HTRF(R) Technology," Journal of Biomolecular Screening, 1999, vol. 4 (6), pp. 309-314.

Miyoshi Y., et al., "Association of Centrosomal Kinase STK15/BTAK mRNA Expression with Chromosomal Instability in Human Breast cancers," International Journal of Cancer, 2001, vol. 92 (3), pp. 370-373.

Moreno B.G., et al., "Differential gene expression profile in endometrioid and nonendometrioid endometrial carcinoma: STK15 is frequently overexpressed and amplified in nonendometrioid carcinomas," Cancer Research, 2003, vol. 63 (18), pp. 5697-5702.

Neben K., et al., ""Microarray-Based Screening for Molecular Markers in Medulloblastoma Revealed STK15 as Independent Predictor for Survival,"" Cancer Research, 2004, vol. 64 (9), pp. 3103-3111.

Nelson R G., et al., "Dicyclic and Tricyclic Diaminopyrimidine Derivatives as Potent Inhibitors of Cryptosporidium Parvum Dihydrofolate Reductase: Structure-Activity and Structure-Selectivity Correlations," Antimicrobial Agents and Chemotheraphy, 2001, vol. 45 (12), pp. 3293-3303.

Nishida N., et al., ""High Copy Amplification of the Aurora-A Gene is Associated with Chromosomal Instability Phenotype in Human Colorectal Cancers,"" Cancer Biology and Therapy, 2007, vol. 6 (4), pp. e1-e9.

Office Action mailed Jan. 31, 2011 for U.S. Appl. No. 12/623,026, filed Nov. 20, 2009.

Qi G., et al., "Aurora-B Expression and its Correlation with Cell Proliferation and Metastasis in Oral Cancer," Virchows Arch, 2007, vol. 450 (3), pp. 297-302.

Reichardt W., et al., "The Putative Serine/threonine Kinase Gene STK15 on Chromosome 20q13.2 is Amplified in Human Gliomas," Molecular Endocrinology, 2003, vol. 10 (5), pp. 1275-1279.

Reiter R., et al., "Aurora Kinase A Messenger RNA Overexpression is Correlated with Tumor Progression and Shortened Survival in Head and Neck Squamous Cell Carcinoma," Clinical cancer Research, 2006, vol. 12 (17), pp. 5136-5141.

Riley R.J., et al., "Time-Dependent CYP Inhibition," Expert Opin Drug Metab Toxicol, 2007, vol. 3 (1), pp. 51-66.

Rosowsky A., et al., "2,4-Diaminothieno[2,3-d]Pyrimidines as Antifolates and Antimalarials. 3. Synthesis of 5,6-Disubstituted Deriviates and Related Tetracyclic Analogs," Journal of Medicinal Chemistry, 1973, vol. 16 (3), pp. 191-194.

Roth B., "2,4-Diaminopyrimidines. The Cyclization of 6-Phenacylthio and Related Derivates to Thieno[2,3-d]Pyrimidines and Thiazolo[3,2-c]Pyrimidines," Journal of Medicinal Chemistry, 1969, vol. 12 (2), pp. 227-232.

(56) References Cited

OTHER PUBLICATIONS

Roth B., et al., "The Protonation of 2,4-Diaminopyrimidines. I. Dissociation Constants and Substituent Effects," The Journal of Organic Chemistry, 1969, vol. 34 (4), pp. 821-836.

Royce M.E., et al., "STK15/Aurora-A expression in primary breast tumors is correlated with nuclear grade but not with prognosis," Cancer, 2004, vol. 100 (1), pp. 12-19.

Sen S., et al., "A Putative Serine/Threonine Kinase Encoding Gene BTAK on Chromosome 20q13 is Amplified and Overexpressed in Human Breast Cancer Cell Lines," Oncogene, 1997, vol. 14 (18), pp. 2195-2200.

Sen S., et al., "Amplification/Overexpression of a Mitotic Kinase Gene in Human Bladder Cancer," Journal of the National Cancer Institute, 2002, vol. 94 (17), pp. 1320-1329.

Sherif S.M., et al., "Syntheses with Heterocyclic Beta-Enaminonitriles: An Expeditious Synthetic Approach to Polyfunctionally Substituted 5-Phenyl-Sulfonylthiophenes and their Fused Derivates," Monatshefte fur Chemie Chemical Monthly , 1997, vol. 128, pp. 687-696.

Smith S.L., et al., "Overexpression of Aurora B Kinase (AURKB) in Primary Non-Small Cell Lung Carcinoma Is Frequent, Generally Driven from One Allele, and Correlates with the Level of Genetic Instability," British Journal of Cancer, 2005, vol. 93 (6), pp. 719-729.

Sorrentino R., et al., "Aurora B Overexpression Associates with the Thyroid Carcinoma Undifferentiated Phenotype and is Required for Thyroid Carcinoma Cell Proliferation," The Journal of Clinical Endocrinology and Metabolism, 2005, vol. 90 (2), pp. 928-935.

Tanaka T., et al., "Centrosomal Kinase AIK1 is Overexpressed in Invasive Ductal Carcinoma of the Breast," Cancer Research, 1999, vol. 59 (9), pp. 2041-2044.

Tatsuka M., et al., "Overexpression of Aurora-A potentiates HRAS-mediated Oncogenic Transformation and Is Implicated in Oral Carcinogenesis ," Oncogene, 2005, vol. 24 (6), pp. 1122-1127.

Taylor E.C., et al., "Synthesis of Thieno[2,3-d]Pyrimidine Analogues of the Potent Antitumor Agent N-{4-[2-(2-Amino-4(3H)-Oxo-7H-Pyrrolo[2,3-d]Pyrimidin-5-y1)Ethyl]-Benzoy- I}-1-Glutamic Acid (LY231514)," Heterocycles, 1996, vol. 43 (2), pp. 349-365.

Tchatchou S., et al., "Aurora Kinases A and B and Familial Breast Cancer Risk," Cancer Letter, 2007, vol. 247 (2), pp. 266-272.

Tong T., et al., ""Overexpression of Aurora-A Contributes to Malignant Development of Human Esophageal Squamous Cell Carcinoma,"" Clinical Cancer Research, 2004, vol. 10 (21), pp. 7304-7310.

Underiner T.L., et al, "Development of Vascular Endothelial Growth Factor Receptor (VEGFR) Kinase Inhibitors as Anti- Angiogenic Agents in Cancer Therapy," Current Medicinal Chemistry, 2004, vol. 11 (6), pp. 731-745.

Vidarsdottir L., et al., "Breast Cancer Risk Associated with AURKA 91T -> A Polymorphism in Relation to BRCA Mutations," Cancer Letter, 2007, vol. 250 (2), pp. 206-212.

Vischioni B., et al., "Frequent Overexpression of Aurora B Kinase, a Novel Drug Target, in Non-Small Cell lung Carcinoma Patients," Molecular cancer Therapeutics, 2006, vol. 5 (11), pp. 2905-2913.

Walsby E., et al., "Effects of the Aurora Kinase Inhibitors AZD1152-HQPA and ZM447439 on Growth Arrest and Polyploidy in Acute Myeloid Leukemia Cell Lines and Primary Blasts," Haematologica, 2008, vol. 93 (5), pp. 662-669.

Xu H.T., et al., "Expression of Serine Threonine Kinase 15 is Associated with Poor differentiation in Lung Squamous Cell Carcinoma and Adenocarcinoma," Pathology International, 2006, vol. 56 (7), pp. 375-380.

Yang S.B., et al., "Amplification and Overexpression of Aurora-A in Esophageal Squamous Cell Carcinoma," Oncology Reports, 2007, vol. 17 (5), pp. 1083-1088.

Zeng W.F., et al., "Aurora B Eexpression Correlates with Aggressive Behaviour in Glioblastoma Multiforme," Journal og Clinical Pathology, 2007, vol. 60 (2), pp. 218-221.

Zhoa X., et al., "[Mutation of p53 and Overexpression of STK15 in Laryngeal Squamous-Cell Carcinoma]," Chinese Journal of Oncology, 2005, vol. 27 (3), pp. 134-137.

Zhou S., et al., "Mechanism-Based Inhibition of Cytochrome P450 3A4 by Therapeutic Drugs," Clin Pharmacokinet, 2005, vol. 44 (3), pp. 279-304.

Zhu J., et al., "AURKA Amplification, Chromosome Instability, and Centrosome Abnormality in Human Pancreatic Carcinoma Cells," Cancer Genet Cytogenet, 2005, vol. 159 (1), pp. 10-17.

Zimmermann K., et al., "Balancing Oral Exposure with Cyp3A4 Inhibition in Benzimidazole-based IGF-IR Inhibitors," Bioorganic and Medicinal Chemistry Letters, 2008, vol. 18 (14), pp. 4075-4080.

THIENO[3,2-C]PYRIDINE KINASE INHIBITORS WITH IMPROVED CYP SAFETY PROFILE

CROSS-REFERENCE TO RELATED APPLICATIONS

This application is a continuation of U.S. application Ser. No. 12/632,183, filed Dec. 7, 2009, which claims priority to provisional application Ser. No. 61/120,281, filed Dec. 5, 2008, and provisional application Ser. No. 61/223,760, filed Jul. 8, 2009.

FIELD OF THE INVENTION

This invention pertains to compounds that inhibit protein kinases such as Aurora-kinases and the VEGFR and PDGFR families of kinases, and which have an improved safety profile due to low CYP3A4 inhibition, compositions containing the compounds, and methods of treating diseases using the compounds.

BACKGROUND OF THE INVENTION

Mitosis is a process by which a complete copy of a duplicated genome is segregated by the microtuble spindle apparatus into two daughter cells. Aurora-kinases, key mitotic regulators required for genome stability, have been found to be overexpressed in human tumors. There is therefore an existing need in the therapeutic arts for compounds which inhibit Aurora-kinases, compositions comprising the inhibitors and methods of treating diseases during which Aurora-kinases are unregulated or overexpressed.

The reversible phosphorylation of proteins is one of the primary biochemical mechanisms mediating eukaryotic cell signaling. This reaction is catalyzed by protein kinases that transfer the g-phosphate group of ATP to hydroxyl groups on target proteins. 518 such enzymes exist in the human genome of which ~90 selectively catalyze the phosphorylation of tyrosine hydroxyl groups Cytosolic tyrosine kinases reside intracellularly whereas receptor tyrosine kinases (RTKs) possess both extracellular and intracellular domains and function as membrane spanning cell surface receptors. As such, RTKs mediate the cellular responses to environmental signals and facilitate a broad range of cellular processes including proliferation, migration and survival.

RTK signaling pathways are normally highly regulated, yet their over-activation has been shown to promote the growth, survival and metastasis of cancer cells. Dysregulated RTK signaling occurs through gene over-expression or mutation and has been correlated with the progression of various human cancers.

The VEGF receptor (VEGFR) family consists of three RTKs, KDR (kinase insert domain-containing receptor; VEGFR2), FLT1 (Fms-like tyrosine kinase; VEGFR1), and FLT4 (VEGFR3). These receptors mediate the biological function of the vascular endothelial growth factors (VEGF-A, -B, C, -D, -E and placenta growth factor (PlGF)), a family of homodimeric glycoproteins that bind the VEGF receptors with varying affinities.

KDR is the major mediator of the mitogenic, angiogenic and permeability-enhancing effects of VEGF-A, hereafter referred to as VEGF. Many different cell types are able to produce VEGF, yet its biological activity is limited predominately to the vasculature by way of the endothelial cell-selective expression of KDR. Not surprisingly, the VEGF/KDR axis is a primary mediator of angiogenesis, the means by which new blood vessels are formed from preexisting vessels.

FLT1 binds VEGF, VEGF-B and placental growth factor. FLT1 is expressed on the surface of smooth muscle cells, monocytes and hematopoietic stems cells in addition to endothelial cells. Activation of FLT1 signaling results in the mobilization of marrow-derived endothelial progenitor cells that are recruited to tumors where they contribute to new blood vessel formation.

FLT4 mediates the signaling of VEGF-C and VEGF-D, which mediate formation of tumor-associated lymphatic vessels (lymphangiogenesis). Lymphatic vessels are one of the routes by which cancer cells disseminate from solid tumors during metastasis.

The PDGF receptor (PDGFR) family consists of five RTK's, PDGFR-a and -b, CSF1R, KIT, and FLT3.

The a and b isoforms of the platelet-derived growth factor (PDGF) receptors occur as homodimers or a/b heterodimers and are found most commonly on the surface of fibroblasts and smooth muscle cells. PDGFR-b contributes to tumor angiogenesis through the proliferation and migration of pericytes, the peri-endothelial cells that associate with and stabilize immature blood vessels. In gliomas, autocrine PDGFR stimulation, brought about by the co-expression of PDGF and PDGF receptors, mediates tumor cell proliferation and survival.

CSF-1R is encoded by the cellular homolog of the retroviral oncogene v-fms and is a major regulator of macrophage development. Macrophages are frequent components of tumor stroma and have been shown to modify the extracellular matrix in a manner beneficial to tumor growth and metastasis.

KIT is expressed by hematopoietic progenitor cells, mast cells, germ cells and by pacemaker cells in the gut (interstitial cells of Cajal). It contributes to tumor progression by two general mechanisms namely autocrine stimulation by its ligand, stem cell factor (SCF), and through mutations that result in ligand-independent kinase activity.

FLT3 is normally expressed on hematopoietic stem cells where its interaction with FLT3 ligand (FL) stimulates stem cell survival, proliferation and differentiation. In addition to being over-expressed in various leukemia cells, FLT3 is frequently mutated in hematological malignancies with approximately one-third of patients with acute myeloid leukemia (AML) harboring activating mutations.

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

Administered drugs are eliminated from the body either by excretion or by metabolism to one or more metabolites. One class of metabolizing enzymes that is particularly important in the metabolism of drugs is the cytochrome P450 (also known as CYP or P450) family of enzymes. This is a large family of isoenzymes which has been divided into over 15 subfamilies. The CYP3A subfamily, which includes CYP3A4, 3A5, 3A7 and 3A43 is responsible for the metabolism of about 60% of known therapeutic drugs. CYP3A4 in particular is the most abundant CYP isoenzyme in both liver and intestine and is involved in the metabolism of more than 50% of the clinically used drugs (Mechanism-Based Inhibition of Cytochrome P455 3A4 by Therapeutic Drugs. Clin. Pharmacokinet, 2005, 44, 279-304). Like all other CYP enzymes, CYP3A4 is susceptible to both reversible and pseudo-irreversible or irreversible (mechanism based) inhibition (Time-dependent CYP Inhibition. Expert Opin. Drug Metab. Toxicol. 2007, 3, 51-66). Their low substrate specificity makes the CYP enzymes susceptible to inhibition by a wide variety of structurally distinct drugs.

As a result of CYP inhibition, abrupt changes can occur with a co-administered agent in a single individual leading to a substantial increase or decrease in the blood and tissue concentrations of a drug or metabolite. These types of changes can alter a drug's safety and efficacy profile in profound ways, especially drugs with narrow therapeutic windows. As outlined in the FDA guidance to industry, a detailed evaluation of the CYP inhibition potential is required of all new drug candidates (Guidance for Industry. Drug Metabolism/Drug Interaction Studies in the Drug Development Process: Studies in Vitro. US FDA April 1997).

This issue of drug-drug interaction is very important in oncology treatment as patients are typically treated with multiple drugs. Thus, reducing the risk of such interaction is an important consideration in the development of novel cancer therapeutics.

While thienopyridine compounds disclosed in WO2005/010009 display potent inhibition of Aurora and PDGFR/VEGFR kinases, they may also be inhibitors of CYP3A4. This invention pertains to novel thienopyridines of formula I, which maintain potent inhibition of both Aurora kinases and the family of kinases encompassing PDGFR and VEGFR and also demonstrate at least a 10-30 fold reduction in CYP3A4 inhibition. Because the compounds of the present invention have significantly reduced CYP3A4 inhibition, they are expected to display low drug-drug interaction liability.

In addition to the reduction in CYP inhibition, the compounds of the invention have demonstrated their utility in additional assays utilized to assess the suitability of the compounds as drug candidates. For instance, the compounds of the invention demonstrate potency in whole cell assays (e.g., in the Human Umbilical Vein Endothelial Cell (HUVEC) assay and the assay measuring histone D3 phosphorylation and induction of polyploidy) and suitable pharmokinetic properties (e.g., oral clearance and oral bioavailability), in vivo efficacy (e.g., Uterine Edema model, rodent flank and orthotopic tumor models), cardiovascular safety, CNS assessments and gastrointestinal assays.

SUMMARY OF THE INVENTION

In one embodiment, the present invention provides compounds of formula (I)

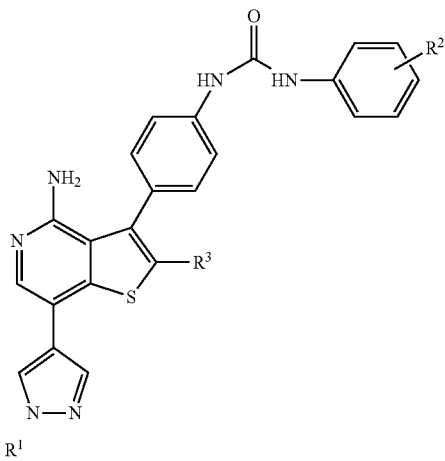

wherein
$R^1$ is hydroxyalkyl;
$R^2$ is selected from the group consisting of alkoxy, alkyl, halo, and haloalkoxy; and
$R^3$ is hydrogen or alkyl.

Still another embodiment pertains to methods of treating diseases involving mediation, overexpression or disregulation of kinases in a mammal, the methods comprising administering thereto a therapeutically effective amount of a compound having Formula I,

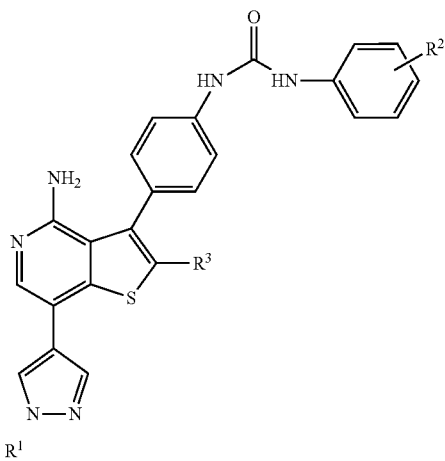

wherein
$R^1$ is hydroxyalkyl;
$R^2$ is selected from the group consisting of alkoxy, alkyl, halo, and haloalkoxy; and
$R^3$ is hydrogen or alkyl.

Another embodiment pertains to methods of treating acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myeloegeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor in a mammal, the methods comprising administering thereto a therapeutically effective amount of a compound of formula I, alone or in combination with radiotherapy.

Another embodiment pertains to methods of treating acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor in a mammal, the methods comprising administering thereto a therapeutically effective amount of N-(4-{4-amino-7-[1-(2-hydroxyethyl)-1H-pyrazol-4-yl]thieno[3,2-c]pyridin-3-yl}phenyl)-N'-(3-fluorophenyl)urea, alone or in combination with radiotherapy.

Another embodiment pertains to methods of treating acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor in a mammal, the methods comprising administering thereto a therapeutically effective amount of N-(4-[4-amino-7-[1-(2-hydroxyethyl)-1H-pyrazol-4-yl]thieno[3,2-c]pyridin-3-yl]phenyl)-N'-[4-(difluoromethoxy)phenyl]urea, alone or in combination with radiotherapy.

Another embodiment pertains to methods of treating acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor in a mammal, the methods comprising administering thereto a therapeutically effective amount of N-[4-(4-amino-7-{1-[(2S)-2-hydroxypropyl]-1H-pyrazol-4-yl}thieno[3,2-c]pyridin-3-yl)phenyl]-N'-(3-methylphenyl)urea, alone or in combination with radiotherapy.

Another embodiment pertains to methods of treating acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myeleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor in a mammal, the methods comprising administering thereto a therapeutically effective amount of N-(4-{4-amino-7-[1-(2-hydroxy-2-methylpropyl)-1H-pyrazol-4-yl]thieno[3,2-c]pyridin-3-yl}phenyl)-N'-(4-methoxyphenyl)urea, alone or in combination with radiotherapy.

Another embodiment pertains to methods of treating acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myeleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor in a mammal, the methods comprising administering thereto a therapeutically effective amount of N-[4-(4-amino-7-{1-[(2S)-2,3-dihydroxypropyl]-1H-pyrazol-4-yl}thieno[3,2-c]pyridin-3-yl)phenyl]-N'-(4-methoxyphenyl)urea, alone or in combination with radiotherapy.

Another embodiment pertains to compositions comprising an excipient and a therapeutically effective amount of a compound of formula I, and a therapeutically effective amount of one additional therapeutic agent or more than one additional therapeutic agent.

Another embodiment pertains to compositions comprising an excipient and a therapeutically effective amount of N-(4-{4-amino-7-[1-(2-hydroxyethyl)-1H-pyrazol-4-yl]thieno[3,2-c]pyridin-3-yl}phenyl)-N'-(3-fluorophenyl)urea, and a therapeutically effective amount of one additional therapeutic agent or more than one additional therapeutic agent.

Another embodiment pertains to compositions comprising an excipient and a therapeutically effective amount of N-(4-{4-amino-7-[1-(2-hydroxyethyl)-1H-pyrazol-4-yl]thieno[3,2-c]pyridin-3-yl}phenyl)-N'-[4-(difluoromethoxy)phenyl]

urea, and a therapeutically effective amount of one additional therapeutic agent or more than one additional therapeutic agent.

Another embodiment pertains to compositions comprising an excipient and a therapeutically effective amount of N-[4-(4-amino-7-{1-[(2S)-2-hydroxypropyl]-1H-pyrazol-4-yl}thieno[3,2-c]pyridin-3-yl)phenyl]-N'-(3-methylphenyl)urea, and a therapeutically effective amount of one additional therapeutic agent or more than one additional therapeutic agent.

Another embodiment pertains to compositions comprising an excipient and a therapeutically effective amount of N-(4-{4-amino-7-[1-(2-hydroxy-2-methylpropyl)-1H-pyrazol-4-yl]thieno[3,2-c]pyridin-3-yl}phenyl)-N'-(4-methoxyphenyl)urea, and a therapeutically effective amount of one additional therapeutic agent or more than one additional therapeutic agent.

Another embodiment pertains to compositions comprising an excipient and a therapeutically effective amount of a N-[4-(4-amino-7-{1-[(2S)-2,3-dihydroxypropyl]-1H-pyrazol-4-yl}thieno[3,2-c]pyridin-3-yl)phenyl}-N'-(4-methoxyphenyl)urea, and a therapeutically effective amount of one additional therapeutic agent or more than one additional therapeutic agent.

Still another embodiment pertains to methods of treating diseases involving mediation, overexpression or disregulation of kinases in a mammal, the methods comprising administering thereto a therapeutically effective amount of a compound of formula I, and a therapeutically effective amount of one additional therapeutic agent or more than one additional therapeutic agent alone or in combination with radiotherapy.

Still another embodiment pertains to methods of treating diseases involving mediation, overexpression or disregulation of kinases in a mammal, the methods comprising administering thereto a therapeutically effective amount of N-(4-{4-amino-7-[1-(2-hydroxyethyl)-1H-pyrazol-4-yl]thieno[3,2-c]pyridin-3-yl}phenyl)-N'-(3-fluorophenyl)urea, and a therapeutically effective amount of one additional therapeutic agent or more than one additional therapeutic agent alone or in combination with radiotherapy.

Still another embodiment pertains to methods of treating diseases involving mediation, overexpression or disregulation of kinases in a mammal, the methods comprising administering thereto a therapeutically effective amount of N-(4-{4-amino-7-[1-(2-hydroxyethyl)-1H-pyrazol-4-yl]thieno[3,2-c]pyridin-3-yl}phenyl)-N'-[4-(difluoromethoxy)phenyl]urea, and a therapeutically effective amount of one additional therapeutic agent or more than one additional therapeutic agent alone or in combination with radiotherapy.

Still another embodiment pertains to methods of treating diseases involving mediation, overexpression or disregulation of kinases in a mammal, the methods comprising administering thereto a therapeutically effective amount of N-[4-(4-amino-7-{1-[(2S)-2-hydroxypropyl]-1H-pyrazol-4-yl}thieno[3,2-c]pyridin-3-yl)phenyl]-N'-(3-methylphenyl)urea, and a therapeutically effective amount of one additional therapeutic agent or more than one additional therapeutic agent alone or in combination with radiotherapy.

Still another embodiment pertains to methods of treating diseases involving mediation, overexpression or disregulation of kinases in a mammal, the methods comprising administering thereto a therapeutically effective amount of N-(4-{4-amino-7-[1-(2-hydroxy-2-methylpropyl)-1H-pyrazol-4-yl]thieno[3,2-c]pyridin-3-yl}phenyl)-N'-(4-methoxyphenyl)urea, and a therapeutically effective amount of one additional therapeutic agent or more than one additional therapeutic agent alone or in combination with radiotherapy.

Still another embodiment pertains to methods of treating diseases involving mediation, overexpression or disregulation of kinases in a mammal, the methods comprising administering thereto a therapeutically effective amount of N-[4-(4-amino-7-{1-[(2S)-2,3-dihydroxypropyl]-1H-pyrazol-4-yl}thieno[3,2-c]pyridin-3-yl)phenyl]-N'-(4-methoxyphenyl)urea, and a therapeutically effective amount of one additional therapeutic agent or more than one additional therapeutic agent alone or in combination with radiotherapy.

Another embodiment pertains to methods of treating pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer, the methods comprising administering thereto a therapeutically effective amount of a compound of formula I, alone or in combination with radiotherapy.

Another embodiment pertains to methods of treating pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer, the methods comprising administering thereto a therapeutically effective amount of N-(4-{4-amino-7-[1-(2-hydroxyethyl)-1H-pyrazol-4-yl]thieno[3,2-c]pyridin-3-yl}phenyl)-N'-(3-fluorophenyl)ure, alone or in combination with radiotherapy.

Another embodiment pertains to methods of treating pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer, the methods comprising administering thereto a therapeutically effective amount of N-(4-{4-amino-7-[1-(2-hydroxyethyl)-1H-pyrazol-4-yl]thieno[3,2-c]pyridin-3-yl}phenyl)-N'-[4-(difluoromethoxy)phenyl]urea, alone or in combination with radiotherapy.

Another embodiment pertains to methods of treating pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer, the methods comprising administering thereto a therapeutically effective amount of N-[4-(4-amino-7-{1-[(2S)-2-hydroxypropyl]-1H-pyrazol-4-yl}thieno[3,2-c]pyridin-3-yl)phenyl]-N'-(3-methylphenyl)urea, alone or in combination with radiotherapy.

Another embodiment pertains to methods of treating pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer, the methods comprising administering thereto a therapeutically effective amount of N-(4-{4-amino-7-[1-(2-hydroxy-2-methylpropyl)-1H-pyrazol-4-yl]thieno[3,2-c]pyridin-3-yl}phenyl)-N'-(4-methoxyphenyl)urea, alone or in combination with radiotherapy.

Another embodiment pertains to methods of treating pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer, the methods comprising administering thereto a therapeutically effective amount of N-[4-(4-amino-7-{1-[(2S)-2,3-dihydroxypropyl]-1H-pyrazol-4-yl}thieno[3,2-c]pyridin-3-yl)phenyl]-N'-(4-methoxyphenyl)urea, alone or in combination with radiotherapy.

Still another embodiment pertains to compounds
N-(4-[4-amino-7-[1-(2-hydroxyethyl)-1H-pyrazol-4-yl]thieno[3,2-c]pyridin-3-yl]phenyl)-N'-(3-fluorophenyl) urea;

N-(4-[4-amino-7-[1-(2-hydroxyethyl)-1H-pyrazol-4-yl]thieno[3,2-c]pyridin-3-yl]phenyl)-N'-[4-(difluoromethoxy)phenyl]urea;

N-[4-(4-amino-7-{1-[(2S)-2-hydroxypropyl]-1H-pyrazol-4-yl}thieno[3,2-c]pyridin-3-yl)phenyl]-N'-(3-methylphenyl)urea;

N-(4-{4-amino-7-[1-(2-hydroxy-2-methylpropyl)-1H-pyrazol-4-yl]thieno[3,2-c]pyridin-3-yl}phenyl)-N'-(4-methoxyphenyl)urea; and N-[4-(4-amino-7-{1-[(2S)-2,3-dihydroxypropyl]-1H-pyrazol-4-yl}thieno[3,2-c]pyridin-3-yl)phenyl]-N'-(4-methoxyphenyl)urea and therapeutically acceptable salts thereof.

Still another embodiment pertains to N-(4-{4-amino-7-[1-(2-hydroxyethyl)-1H-pyrazol-4-yl]thieno[3,2-c]pyridin-3-yl}phenyl)-N'-(3-fluorophenyl)urea.

Still another embodiment pertains to N-(4-{4-amino-7-[1-(2-hydroxyethyl)-1H-pyrazol-4-yl]thieno[3,2-c]pyridin-3-yl}phenyl)-N'-[4-(difluoromethoxy)phenyl]urea.

Still another embodiment pertains to N-[4-(4-amino-7-{1-[(2S)-2-hydroxypropyl]-1H-pyrazol-4-yl}thieno[3,2-c]pyridin-3-yl) phenyl]-N'-(3-methylphenyl)urea.

Still another embodiment pertains to N-(4-{4-amino-7-[1-(2-hydroxy-2-methylpropyl)-1H-pyrazol-4-yl]thieno[3,2-c]pyridin-3-yl}phenyl)-N'-(4-methoxyphenyl)urea.

Still another embodiment pertains to N-[4-(4-amino-7-{1-[(2S)-2,3-dihydroxypropyl]-1H-pyrazol-4-yl}thieno[3,2-c]pyridin-3-yl)phenyl]-N'-(4-methoxyphenyl)urea.

Still another embodiment pertains to a compound of formula I, and therapeutically acceptable salts, prodrugs, esters, amides, salts of prodrugs, salts of esters, and salts of amides thereof.

Still another embodiment pertains to N-(4-[4-amino-7-[1-(2-hydroxyethyl)-1H-pyrazol-4-yl]thieno[3,2-c]pyridin-3-yl]phenyl)-N'-(3-fluorophenyl)urea, and therapeutically acceptable salts, prodrugs, esters, amides, salts of prodrugs, salts of esters, and salts of amides thereof.

Still another embodiment pertains to N-(4-[4-amino-7-[1-(2-hydroxyethyl)-1H-pyrazol-4-yl]thieno[3,2-c]pyridin-3-yl]phenyl)-N'-[4-(difluoromethoxy)phenyl]urea, and therapeutically acceptable salts, prodrugs, esters, amides, salts of prodrugs, salts of esters, and salts of amides thereof.

Still another embodiment pertains to N-[4-(4-amino-7-{1-[(2S)-2-hydroxypropyl]-1H-pyrazol-4-yl}thieno[3,2-c]pyridin-3-yl)phenyl]-N'-(3-methylphenyl)urea, and therapeutically acceptable salts, prodrugs, esters, amides, salts of prodrugs, salts of esters, and salts of amides thereof.

Still another embodiment pertains to N-(4-{4-amino-7-[1-(2-hydroxy-2-methylpropyl)-1H-pyrazol-4-yl]thieno[3,2-c]pyridin-3-yl}phenyl)-N'-(4-methoxyphenyl)urea, and therapeutically acceptable salts, prodrugs, esters, amides, salts of prodrugs, salts of esters, and salts of amides thereof.

Still another embodiment pertains to N-[4-(4-amino-7-{1-[(2S)-2,3-dihydroxypropyl]-1H-pyrazol-4-yl}thieno[3,2-c]pyridin-3-yl)phenyl]-N'-(4-methoxyphenyl)urea, and therapeutically acceptable salts, prodrugs, esters, amides, salts of prodrugs, salts of esters, and salts of amides thereof.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof, and that monovalent moieties having more than one atom are attached through their left ends.

It is also meant to be understood that a specific embodiment of a variable moiety may be the same or different as another specific embodiment having the same identifier.

The term "alkoxy," as used herein, refers to an alkyl group attached to the parent molecular moiety through an oxygen atom.

The term "alkyl," as used herein, refers to a group derived from a straight or branched chain saturated hydrocarbon containing from one to ten carbon atoms.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group, as defined herein, substituted with at least one halogen, as defined herein.

The term "hydroxy," as used herein, refers to a —OH group.

The term "hydroxyalkyl," as used herein, refers to an alkyl group substituted with at least one hydroxy group.

The term "KDR" means kinase insert domain receptor (a type III receptor tyrosine kinase) and is also known as FLK1, VEGFR, VEGFR2, and CD309.

The term "VEGFR" means vascular endothelial growth factor receptor.

The term "PDGFR" means platelet-derived growth factor receptor.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

Compounds of this invention containing NH, C(O)OH, OH or SH moieties may have attached thereto prodrug-forming moieties. The prodrug-forming moieties are removed by metabolic processes and release the compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds of this invention produced by in vitro or in vivo metabolic processes, may also have utility for treating diseases associated with overexpression or disregulation of protein kinases.

Certain precursor compounds which may be metabolized in vitro or in vivo to form compounds of this invention may also have utility for treating diseases associated with overexpression or disregulation of protein kinases.

Compounds of this invention may exist as acid addition salts, basic addition salts or zwitterions. Salts of compounds having Formula I are prepared during their isolation or following their purification. Acid addition salts are those derived from the reaction of a compound of this invention with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds of this invention are meant to be embraced by this invention. Basic addition salts of compounds are those derived from the reaction of the compounds of this invention with the bicarbonate, carbonate, hydroxide or phosphate of cations such as lithium, sodium, potassium, calcium and magnesium.

Compounds having Formula I may be administered, for example, bucally, ophthalmically, orally, osmotically, parenterally (intramuscularly, intraperitoneally intrasternally, intravenously, subcutaneously), rectally, topically, transdermally, vaginally and intraarterially as well as by intraarticular injection, infusion, and placement in the body, such as, for example, the vasculature.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a patient in a single dose or in divided doses is from about 0.03 to about 200 mg/kg body weight. Single dose compositions contain these amounts or a combination of submultiples thereof.

Compounds having Formula I may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having Formula I to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having Formula I to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having Formula I to be administered osmotically include, but are not limited to, chlorofluorohydrocarbons, ethanol, water, mixtures thereof and the like. Excipients for preparation of compositions comprising a compound having Formula I to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having Formula I to be administered rectally or vaginally include, but are not limited to, cocoa butter, polyethylene glycol, wax, mixtures thereof and the like.

Compounds having Formula I are expected to be useful when used with alkylating agents, angiogenesis inhibitors, antibodies, antimetabolites, antimitotics, antiproliferatives, aurora kinase inhibitors, other apoptosis promoters (for example, Bcl-xL, Bcl-w and Bfl-1) inhibitors, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, DVD's, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAP's) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteosome inhibitors, purine analogs, pyrimidine analogs, receptor tyrosine kinase inhibitors, retinoids/deltoids plant alkaloids, small inhibitory ribonucleic acids (siRNA's), topoisomerase inhibitors, combinations thereof and the like.

A BiTE antibody is a bi-specific antibody that directs T-cells to attach cancer cells by simultaneously binding the two cells. The T-cell then attacks the target cancer cell. Exemplary BiTE antibodies include adecatumumab (Micromet MT201), blinatumomab (Micromet MT103) and the like.

SiRNA's are molecules having endogenous RNA bases or chemically modified nucleotides. The modifications shall not abolish cellular activity, but rather impart increased stability and/or increased cellular potency. Examples of chemical modifications include phosphorothioate groups, 2'-deoxy-nucleotide, 2'-OCH$_3$-containing ribonucleotides, 2'-F-ribo-nucleotides, 2'-methoxyethyl ribonucleotides or a combination thereof. The siRNA can have varying lengths (10-200 bps) and structures (hairpins, single/double strands, bulges, nicks/gaps, mismatches) and processed in the cell to provide active gene silencing. In certain embodiments, a double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. The multivalent binding protein is preferably engineered to have the three or more antigen binding sites and is generally not a naturally occurring antibody. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific, i.e., capable of binding one antigen or multispecific, i.e., capable of binding two or more antigens. DVD binding proteins comprising two heavy chain DVD polypeptides and two light chain DVD polypeptides are referred to as DVD Ig. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE° (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (metrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Aurora kinase inhibitors include AZD-1152, MLN-8054, VX-680 and the like.

Bcl-2 proteins inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of apoptosis proteins include ApoMab (a fully human affinity-matured IgG1 monoclonal antibody), antibodies that target TRAIL or death receptors (e.g., pro-apoptotic receptor agonists DR4 and DR5), conatumumab, ETR2-ST01, GDC0145, (lexatumumab), HGS-1029, LBY-135, PRO-1762 and tratuzumab.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARD10×ANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxfene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Compounds of this invention can also be used as radiosensitizesr that enhance the efficacy of radiotherapy. Examples of radiotherapy include external beam radiotherapy, teletherapy, brachtherapy and sealed, unsealed source radiotherapy and the like.

Additionally, compounds having Formula I may be combined with other chemptherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECINT™ (rubitecan), OSIDEM® (antibody-based cell drug), OVAREX® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

To determine Aurora B activity of representative compounds of the invention, Active Aurora B enzyme (recombinant residues 1-344) and INCENP (recombinant GST fusion protein (Upstate)) were incubated in wells of a 384 well plate with biotinylted histone H3 peptide residues 1-21 (Upstate), 1 mM ATP, and various concentrations of inhibitors in a HEPES buffer, pH 7.4 containing $MgCl_2$, sodium othrovanadate, and Triton X-100. After 1 hour, the reaction was stopped with EDTA and anti-phospho-histone H3 Europium Cryptate (Cis-Bio) and SA-APC (Phycolink, Prozyme) were added to detect the phosphopeptide. The amount of phosphorylation was determined by the time-resolved fluorescence ratio of signals at 665 nm and 615 nm. The $IC_{50}$'s were calculated by an exponential fit of the inhibition values with the inhibitor concentrations using Assay Explorer software.

To determine Aurora A and C activity of representative compounds of the invention, Active Aurora A or C enzyme was incubated in wells of a 384 well plate with biotinylated STK substrate-2 (Upstate), 1 mM ATP, and various concentrations of inhibitors in a Hepes buffer, pH 7.4 containing $MgCl_2$, sodium othrovanadate, and Triton X-100. After 1 hour, the reaction was stopped with EDTA and anti-phospho-STK antibody Europium Cryptate (Upstate) and SA-XL665 (Upstate) were added to detect the phosphopeptide. The amount of phosphorylation was determined by the time-resolved fluorescence ratio of signals at 665 nm and 615 nm.

The $IC_{50}$s were calculated by an exponential fit of the inhibition values with the inhibitor concentrations using Assay Explorer software.

To determine the activity of the various kinases, a homogenous time-resolved fluorescence (HTRF) in vitro kinase assay was used. (Mathis, G., *HTRF(R) Technology*. J Biomol Screen, 1999. 4(6): p. 309-314; Alfred J. Kolb, Paul V. Kaplita, David J. Hayes, Young-Whan Park, Christine Pernell, John S. Major and Gerard Mathis, *Drug Discovery Today,* 1998, 3, 333-342.)

For example for KDR, cKIT, FLT1, CSF1R and FTL3, purified enzyme was mixed with 0.5 µM N-biotinylated substrate (Biotin-Ahx-AEEEYFFLA-amide (SEQ. ID. 1)), various concentrations of inhibitor in reaction buffer (50 mM HEPES, pH 7.1, 10 mM $MgCl_2$, 2 mM $MnCl_2$, 0.1% BSA and 1 mM DTT, 40 µL final volume), ATP (1 mM final conc.) in a black 384-well plate. After 60 minutes incubation at room temperature, the reaction was quenched by addition of a buffered EDTA solution (final approximate concentrations: 30 mM EDTA, 0.1% BSA, 0.1% Triton X-100 and 0.24M KF) and a solution of revelation agents (to give 0.084 ng/well streptavidin-XL-665 (Cis-Bio) and 6.5 ng/well antiphsophotyrosine mAb PT66-K Europium kryptate) was added to the reaction mixture. The quenched reaction was allowed to stand at room temperature for 3 hours and was then read in a time-resolved fluorescence detector (InVision, Perkin-Elmer) at 620 nm and 665 nm sequentially with excitation. The ratio between the signal of 620 nm and 665 nm was used in the calculation of the $IC_{50}$.

Details for the various kinases are shown in Table I.

TABLE I

| Enzyme | Construct | MW (kD) | HTRF ASSAYS Enz. Reaction Conc. (ng/well) |
|---|---|---|---|
| KDR | His6-KDR 789-1354 | 63 | 7 |
| cKIT | GST-Fusion | 70 | 4 |
| FLT1 | His6-Tag | 65 | |
| CSF-1r | M-His(6)-CSF-1R Q547-C972 | 50 | 10 |
| FLT3 | M-His(6)-FLT3 Q569-S993 | 50 | 0.6 |
| PDGFR-beta | GST-Fusion | 100 | 20 |

Table 2 and Table 3 demonstrate the utility of Examples 1-6 as inhibitors of multiple kinases.

TABLE 2

| | VEGRF family | | PDGFR Family | | |
|---|---|---|---|---|---|
| Example | KDR $IC_{50}$ (µM) | FLT1 $IC_{50}$ (µM) | CSF1R $IC_{50}$ (µM) | FLT3 $IC_{50}$ (µM) | cKIT $IC_{50}$ (µM) |
| 1 | 0.00159 | 0.00125 | 0.00342 | 0.0013 | 0.01953 |
| 2 | 0.00265 | 0.0021 | 0.00222 | 0.00113 | 0.02727 |
| 3 | 0.0016 | 0.00204 | 0.00562 | 0.00218 | 0.02711 |
| 4 | 0.00501 | 0.00429 | 0.00787 | 0.00193 | 0.05305 |
| 5 | 0.00183 | 0.00145 | 0.00134 | 0.00122 | 0.01258 |
| 6 | 0.00218 | 0.0019 | 0.00274 | 0.00181 | 0.00428 |

TABLE 3

| Example | Aurora B $IC_{50}$ (µM) | Aurora A $IC_{50}$ (µM) |
|---|---|---|
| 1 | 0.00673 | 0.67542 |
| 2 | 0.00787 | 4.7431 |
| 3 | 0.01121 | 0.24831 |
| 4 | 0.01484 | 3.61985 |
| 5 | 0.02893 | 0.57014 |
| 6 | 0.00844 | 0.3572 |

CYP 3A4 Assay

Assays (200 µL final volume) were carried out in NUNC polypropylene deep well plates in 50 mM potassium phosphate buffer, pH 7.4, using a microtiter plate shaker in a 37° C. incubator. Pooled human liver microsomes (BD Gentest, 50 µg/mL) were incubated with 5 concentrations of test compound (from 0.1 µM to 10 µM), 1 mM NADPH (Sigma), and 2 µM midazolam (Sigma). A constant amount of dimethylsulfoxide (1%) was added to the incubations with the test compounds, and each analysis was performed in duplicate. For preincubation experiments (Pre), the microsomes, test compounds, and NADPH were mixed and incubated 30 minutes before addition of midazolam. For coincubation experiments (Co), the compounds, microsomes, and midazolam were mixed and the reaction initiated by addition of NADPH to the wells. In both protocols, the complete reaction was terminated after 10 minutes of shaking by addition of 100 µL of a 1/1 mixture of acetonitrile and methanol containing 0.33 µM 1-hydroxytriazolam.

For analysis, an aliquot of each well were transferred to an autosampler vial and 10 µL injected onto a Shimadzu LC-10A HPLC system equipped with a YMC-AQ (2.0×50 mm) column. The components were separated using a gradient of 10% acetonitrile –0.1% acetic acid to 70% acetonitrile –0.1% acetic acid at a flow rate of at 0.4 mL/minute over 5 minutes. Midazolam, 1-hydroxytriazolam (internal standard), 1-hydroxymidazolam and 4-hydroxymidazolam were quantified by LC-MS/MS using an LCQ Duo (ThermoFinnigan). The ratio of 1-hydroxymidazolam (CYP 3A4 product) and the internal standard at each concentration of compound was used to calculate the % inhibition of activity relative to the ratio calculated for control incubations without inhibitor. In the absence of NADPH, no hydroxylation of midazolam was observed. Ketoconazole was used as a standard inhibitor, which at 0.1 µM produces 70-80% inhibition of CYP 3A4. The $IC_{50}$ (the concentration at which 50% of the enzyme is inhibited) was calculated for Examples 1-5 and Example 6 (described as EXAMPLE 703 in WO 2005/10009) and is shown in Table 4 below.

TABLE 4

| | Incubation Conditions | $IC_{50}$ (µM) |
|---|---|---|
| EXAMPLE 1 | Co | >10 |
| | Pre | >10 |
| EXAMPLE 2 | Co | >10 |
| | Pre | >10 |
| EXAMPLE 3 | Co | >10 |
| | Pre | >10 |
| EXAMPLE 4 | Co | >10 |
| | Pre | >10 |
| EXAMPLE 5 | Co | >10 |
| | Pre | >10 |
| EXAMPLE 6 | Co | .30 |
| | Pre | .76 |

The data in tables 2, 3 and 4 illustrate the utility of the compounds of this invention as inhibitors of multiple kinases with the added benefit of reduced CYP inhibition.

Compounds described as having low CYP inhibition or as not inhibiting CYP are those compounds with an $IC_{50}$ of >10 µM in the above assay.

The structural homology between Aurora Protein Kinases A, B and C is reported in Nature Reviews/Cancer, Vol. 4 December, 2004.

It is expected that, because the compound of this invention inhibits the activity of Aurora-kinase B, it could also have utility as an inhibitor of protein kinases having close structural homology thereto, such as, for example, Aurora-kinase A and Aurora-kinase C.

Data for Example 1 is shown in Table 5.

TABLE 5

| Example | Aurora B HTRF $IC_{50}$ (µM) | Aurora A HTRF $IC_{50}$ (µM) | Aurora C HTRF $IC_{50}$ (µM) |
| --- | --- | --- | --- |
| 1 | 0.007 | 0.120 | 0.001 |

This data demonstrates the utility of Example 1 as an inhibitor of Aurora-kinase A and Aurora-kinase B and Aurora-kinase C.

Accordingly, compounds of this invention are expected to have utility in treatment of diseases during which protein kinases such as any or all Aurora-kinase family members are expressed.

Involvement of Aurora Kinase in pancreatic carcinoma cells is reported in Zhu, J., et al., AURKA Amplification, Chromosome Instability, And Centrosome Abnormality in Human Pancreatic Carcinoma Cells. Cancer Genet. Cytogenet., 2005. 159(1): p. 10-17; and Li D., Zhu J., Firozi P. F., et al. Overexpression of Oncogenic STK15/BTAK/Aurora A Kinase in Human Pancreatic Cancer. Clin. Cancer Res. 2003; 9:991-7.

Involvement of Aurora Kinase in non-small cell lung carcinoma is reported in Smith, S. L., et al., Overexpression of Aurora B Kinase (AURKB) in Primary Non-Small Cell Lung Carcinoma is Frequent, Generally Driven from One Allele, and Correlates with the Level of Genetic Instability. Br. J. Cancer, 2005. 93(6): p. 719-729.

Involvement of Aurora Kinase in prostate cancer is reported in Chieffi, P., et al., Aurora B Expression Directly Correlates with Prostate Cancer Malignancy. Prostate, 2006. 66(3): p. 326-33; and Chieffi P., Cozzolino L., Kisslinger A., et al. Aurora B Expression Directly Correlates with Prostate Cancer Malignancy and Influences Prostate Cell Proliferation. Prostate 2006; 66:326-33.

Involvement of Aurora Kinase in head and neck squamous cell carcinoma is reported in Reiter, R., et al., Aurora Kinase A Messenger RNA Overexpression is Correlated with Tumor Progression and Shortened Survival in Head and Neck Squamous Cell Carcinoma. Clin Cancer Res, 2006. 12(17): p. 5136-41.

Involvement of Aurora Kinase in acute myeloid leukemia is reported in Walsby E., Walsh V., Pepper C., Burnett A., and Mills K. Haematologica. 2008 May; 93(5):662-9.

Involvement of Aurora Kinase in breast cancer is reported in Tanaka T., Kimura M., Matsunaga K., Fukada D., Mori H., Okano Y. Centrosomal Kinase AIK1 is Overexpressed in Invasive Ductal Carcinoma of The Breast. Cancer Res. 1999; 59:2041-4; Miyoshi Y., Iwao K., Egawa C., Noguchi S. Association of Centrosomal Kinase STK15/BTAK Mrna Expression with Chromosomal Instability in Human Breast Cancers. Int. J. Cancer 2001; 92:370-3; Hogue A., Carter J., Xia W., et al. Loss Of Aurora A/STK15/BTAK Overexpression Correlates with Transition of in Situ to Invasive Ductal Carcinoma of the Breast. Cancer Epidemiol. Biomarkers Prev. 2003; 12:1518-22; Royce M. E., Xia W., Sahin A. A., et al. STK15/Aurora-A Expression in Primary Breast Tumors is Correlated with Nuclear Grade But Not With Prognosis. Cancer 2004; 100:12-9; Bodvarsdottir S. K., Hilmarsdottir H., Birgisdottir V., Steinarsdottir M., Jonasson J. G., Eyfjord J. E., Aurora-A Amplification Associated with BRCA2 Mutation in Breast Tumours. Cancer Lett 2007; 248:96-102; Sen S., Zhou H., White R. A., A Putative Serine/Threonine Kinase Encoding Gene BTAK on Chromosome 20q13 is Amplified and Overexpressed in Human Breast Cancer Cell Lines. Oncogene 1997; 14:2195-200; Lo Y. L., Yu J. C., Chen S. T., et al. Breast Cancer Risk Associated with Genotypic Polymorphism of the Mitosisregulating Gene Aurora-A/STK15/BTAK. In. J. Cancer 2005; 115:276-83; Vidarsdottir L., Bodvarsdottir S. K., Hilmarsdottir H., Tryggvadottir L., Eyfjord J. E., Breast Cancer Risk Associated with AURKA 91T a Polymorphismin Relation to BRCA Mutations. Cancer Lett 2007; 250:206-12; Cox D. G., Hankinson S. E., Hunter D. J., Polymorphisms of the Aurka (STK15/Aurora Kinase) Gene and Breast Cancer Risk (United States). Cancer Causes Control 2006; 17:81-3; and Tchatchou S., Wirtenberger M., Hemminki K., et al. Aurora Kinases A and B and Familial Breast Cancer Risk. Cancer Lett 2007; 247:266-72.

Involvement of Aurora Kinase in lung cancer is reported in Smith S. L., Bowers N. L., Betticher D. C., et al. Overexpression Of Aurora B Kinase (AURKB) in Primary Non small Cell Lung Carcinoma is Frequent, Generally Driven Fromone Allele, and Correlates with the Level Of Genetic Instability. Br. J. Cancer 2005; 93:719-29; Xu H. T., Ma L., Qi F. J., et al. Expression of Serine Threonine Kinase15 is Associated with Poor Differentiation in Lung Squamous Cell Carcinoma and Adenocarcinoma. Pathol. Int. 2006; 56:375-80; Vischioni B., Oudejans J. J., Vos W., Rodriguez J. A., Giaccone G. Frequent Overexpression of Aurora B Kinase, a Novel Drug Target, in Non-Small Cell Lung Carcinoma Patients. Mol. Cancer. Ther. 2006; 5:2905-13; and Gu J., Gong Y., Huang M., Lu C., Spitz M. R., Wu X. Polymorphisms Of STK15 (Aurora-A) Gene and Lung Cancer Risk in Caucasians. Carcinogenesis 2007; 28:350-5.

Involvement of Aurora Kinase in bladder cancer is reported in Comperat E., Camparo P., Haus R., et al. Aurora-A/STK-15 is a Predictive Factor for Recurrent Behaviour in Non-Invasive Bladder Carcinoma: A Study Of 128 Cases of Non-Invasive Neoplasms. Virchows Arch 2007; 450:419-24; Fraizer G. C., Diaz M. F., Lee I. L., Grossman H. B., Sen S. Aurora-A/STK15/BTAK Enhances Chromosomal Instability in Bladder Cancer Cells. Int. J. Oncol. 2004; 25:1631-9; and Sen S., Zhou H., Zhang R. D., et al. Amplification/Overexpression of A Mitotic Kinase Gene in Human Bladder cancer. J. Natl. Cancer Inst. 2002; 94:1320-9.

Involvement of Aurora Kinase in esophageal cancer is reported in Tong T., Zhong Y., Kong J., et al. Overexpression of Aurora-A Contributes to Malignant Development of Human Esophageal Squamous Cell Carcinoma. Clin. Cancer Res. 2004; 10:7304-10; Yang S. B., Zhou X. B., Zhu H. X., et al. Amplification and Overexpression of Aurora-A in Esophageal Squamous Cell Carcinoma. Oncol. Rep. 2007; 17:1083-8; and Kimura M. T., Mori T., Conroy J., et al. Two Functional Coding Single Nucleotide Polymorphisms in STK15 (Aurora-A) Coordinately Increase Esophageal Cancer Risk. Cancer Res 2005; 65:3548-54.

Involvement of Aurora Kinase in brain cancer is reported in Araki K., Nozaki K., Ueba T., Tatsuka M., Hashimoto N. High Expression of Aurora-B/Aurora and Ipll-Like Midbody-Associated Protein (AIM-1) in Astrocytomas. J. Neurooncol. 2004; 67:53-64; Zeng W. F., Navaratne K., Prayson R. A., Weil R. J. Aurora B Expression Correlates with Aggressive Behaviour in Glioblastoma Multiforme. J. Clin. Pathol. 2007; 60:218-21; Reichardt W., Jung V., Brunner C., et al. The Putative Serine/Threonine Kinase Gene STK15 on Chromosome 20q13.2 is Amplified In Human Gliomas. Oncol. Rep. 2003; 10:1275-9; Klein A., Reichardt W., Jung V., Zang K. D., Meese E., Urbschat S. Overexpression and Amplification of STK15 Inhuman Gliomas. Int. J. Oncol. 2004; 25:1789-94; and Neben K., Korshunov A., Benner A., et al. Microarray Based Screening for Molecular Markers Nmedulloblastoma Revealed STK15 as Independent Predictor for Survival. Cancer Res 2004; 64:3103-11.

Involvement of Aurora Kinase in liver cancer is reported in Jeng Y. M., Peng S. Y., Lin C. Y., Hsu H. C. Overexpression and Amplification of Aurora-A in Hepatocellular Carcinoma. Clin. Cancer Res. 2004; 10:2065-71.

Involvement of Aurora Kinase in head and neck cancer is reported in Zhao X., Li F. C., Li Y. H., et al. [Mutation of p53 and Overexpression Of STK15 in Laryngeal Squamous-Cell Carcinoma]. Zhonghua Zhong Liu Za Zhi 2005; 27:134-7; Li F. C., Li Y. H., Zhao X., et al. [Deletion of p15 and p16 Genes and Overexpression of STK15 Gene in Human Laryngeal Squamous Cell Carcinoma]. Zhonghua Yi Xue Za Zhi 2003; 83:316-9; Reiter R., Gais P., Jutting U., et al. Aurora Kinase A Messenger RNA Overexpression is Correlated with Tumor Progression and Shortened Survival in Head and Neck Squamous Cell Carcinoma. Clin. Cancer Res. 2006; 12:5136-41; Qi G., Ogawa I., Kudo Y., et al. Aurora-B Expression and Its Correlation with Cell Proliferation and Metastasis in Oral Cancer. Virchows Arch 2007; 450:297-302; and Tatsuka M., Sato S., Kitajima S., et al. Overexpression of Aurora-A Potentiates HRAS-mediated Oncogenic Transformation and is Implicated in Oral Carcinogenesis. Oncogene 2005; 4:1122-7.

Involvement of Aurora Kinase in thyroid cancer is reported in Sorrentino R., Libertini S., Pallante P. L., et al. Aurora B Overexpression Associates with the Thyroid Carcinoma Undifferentiated Phenotype and is Required for Thyroid Carcinoma Cell Proliferation. J. Clin. Endocrinol. Metab. 2005; 90:928-35.

Involvement of Aurora Kinase in ovarian cancer is reported in Lassmann S., Shen Y., Jutting U., et al. Predictive Value of Aurora-A/STK15 Expression for Late Stage Epithelial Ovarian Cancer Patients Treated By Adjuvant Chemotherapy. Clin Cancer Res 2007; 13:4083-91; and Landen C. N., Jr., Lin Y. G., Immaneni A., et al. Overexpression of the Centrosomal Protein Aurora-A Kinase is Associated with Poor Prognosis in Epithelial Ovarian Cancer Patients. Clin. Cancer Res. 2007; 13:4098-104.

Involvement of Aurora Kinase in renal cancer is reported in Kurahashi T., Miyake H., Hara I., Fujisawa M. Significance of Aurora-A Expression in Renal Cell Carcinoma. Urol. Oncol. 2007; 25:128-33.

Involvement of Aurora Kinase in endometrium cancer is reported in Moreno-Bueno G., Sanchez-Estevez C., Cassia R., et al. Differential Gene Expression Profile in Endometrioid and Nonendometrioid Endometrial Carcinoma:STK15 is Frequently Overexpressed and Amplified in Nonendometrioid Carcinomas. Cancer Res. 2003; 63:5697-702.

Involvement of Aurora Kinase in gastric cancer is reported in Ju H., Cho H., Kim Y. S., et al. Functional Polymorphism 57Val>Ile of Aurora Kinase A Associated with Increased Risk of Gastric Cancer Progression. Cancer Lett. 2006; 242:273-9.

Involvement of Aurora Kinase in colon cancer is reported in Nishida N., Nagasaka T., Kashiwagi K., Boland C. R., Goel A. High Copy Amplification of the Aurora-A Gene is Associated with Chromosomal Instability Phenotype in Human Colorectal Cancers. Cancer Biol. Ther. 2007; 6:525-33; Bischoff J. R., Anderson L., Zhu Y., et al. A Homologue of *Drosophila* Aurora Kinase is Oncogenic and Amplified In Human Colorectal Cancers. EMBO J. 1998; 17:3052-65; Chen J., Sen S., Amos C. I., et al. Association Between Aurora-A Kinase Polymorphisms and Age of Onset of Hereditary Nonpolyposis Colorectal Cancer in a Caucasian Population. Mol. Carcinog. 2007; 46:249-56; Hienonen T., Salovaara R., Mecklin J. P., Jarvinen H., Karhu A., Aaltonen L. A. Preferential Amplification of AURKA 91A (Ile31) in Familial Colorectal Cancers. Int. J. Cancer 2006; 118:505-8; and Ewart-Toland A., Briassouli P., de Koning J. P., et al. Identification of Stk6/STK15 as a Candidate Low-Penetrance Tumor-Susceptibility Gene in Mouse and Human. Nat. Genet. 2003; 34:403-12.

Involvement of Aurora Kinase in cancer is reported in Lin, Y. S., et al., Gene Expression Profiles of the Aurora Family Kinases. Gene Expr., 2006. 13(1): p. 15-26; and Ewart-Toland A., Dai Q., Gao Y. T., et al. Aurora-A/STK15 T+91A is a General Low Penetrance Cancer Susceptibility Gene: A Meta-Analysis of Multiple Cancer Types. Carcinogenesis 2005; 26:1368-73.

Involvement of KDR (VEGFR2) in cancer and studies using VEGF-targeted therapy is reported in Ellis, Lee M., Hicklin, Daniel J. VEGF-Targeted Therapy: Mechanisms Of Anti-Tumor Activity. Nature Reviews Cancer 2008; 8:579-591.

Involvement of Aurora-kinases in bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer is reported in Nature Reviews/Cancer, Vol. 4 December, 2004.

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary. For example, the coupling reaction between 3-bromothieno[3,2-c]pyridin-4-amine and the substituted 4,4,5,5-tetramethyl-2-phenyl-1,3,2-dioxaborolane can be performed prior to or after the formation of the urea linkage.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl(phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$ and $K_2SO_4$); AIBN means 2,2'-azobis(2-methylpropionitrile); 9-BBN means 9-borabicyclo(3.3.1)nonane; Cp means cyclopentadiene; $(DHQD)_2PHAL$ means hydroquinidine 1,4-phthalazinediyl diethyl ether; DBU means 1,8-diazabicyclo(5.4.0)undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppa means diphenylphosphoryl azide; dppb means 1,4-bis(diphenylphosphino)butane; dppe means 1,2-bis(diphenylphosphino)ethane; dppf means 1,1'-bis(diphenylphosphino)ferrocene; dppm means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; HOAT means 1-hydroxy-7-azabenzotriazole; IPA means isopropyl alcohol; LDA means lithium diisopropylamide; LHMDS means lithium bis(hexamethyldisilylamide); MP-$BH_3$ means macroporus triethylammonium methylpolystyrene cyanoborohydride; LAH means lithium aluminum hydride; NCS means N-chlorosuccinimide; PyBOP means benzotriazol-1-yloxytripyrrolidinophosphonium hexafluorophosphate; TBTU means O-benzotriazol-1-yl-N,N,N',N'-tetramethyluronium tetrafluoroborate; TDA-1 means tris(2-(2-methoxyethoxy)ethyl)amine; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

EXAMPLE 1

N-(4-{4-amino-7-[1-(2-hydroxyethyl)-1H-pyrazol-4-yl]thieno[3,2-c]pyridin-3-yl}phenyl)-N'-(3-fluorophenyl)urea

EXAMPLE 1A

3-(4-aminophenyl)-7-iodothieno[3,2-c]pyridin-4-amine

A suspension of 3-bromothieno[3,2-c]pyridin-4-amine (13.7 g, 59.7 mmol), tert-butyl 4-(4,4,5,5-tetramethyl-1,3,2-dioxaborolan-2-yl)phenylcarbamate (20 g, 62.7 mmol), tetrakis(triphenylphosphine)palladium(0) (2.5 g, 2.1 mmol) and $Na_2CO_3$ (13.3 g, 125 mmol) in tetrahydrofuran (150 mL), methanol (40 mL) and water (80 mL) was degassed, then stirred at reflux overnight. The reaction mixture was cooled to room temperature, then partitioned between ethyl acetate and water. The aqueous layer was extracted with additional ethyl acetate and the combined organics were dried (using $MgSO_4$), filtered and the filtrate was concentrated. The residue was purified via silica gel chromatography eluting with 50 to 70% ethyl acetate-hexanes to give crude tert-butyl 4-(4-aminothieno[3,2-c]pyridin-3-yl)phenylcarbamate. A solution of the crude product (59.7 mmol based on 100% yield) in N,N-dimethylformamide (80 mL) was treated with N-iodosuccinimide (13.5 g, 59.7 mol-added in portions) and the resulting dark solution was stirred at room temperature for 2 hours, then partitioned between water (500 mL) and ethyl acetate (100 mL) with NaCl added to facilitate layer separation. The aqueous layer was extracted with additional ethyl acetate (2×75 mL) and the combined organics were washed with sodium thiosulfate (3×20 mL) and brine (50 mL), and then dried (using $MgSO_4$), filtered, and concentrated. The crude material was treated with TFA (20 mL) and $CH_2Cl_2$ (5 mL), stirred at room temperature for 2 hours, concentrated under a stream of nitrogen, then concentrated in vacuo. The solid was dissolved in water (100 mL), carefully treated with solid $Na_2CO_3$ until gas evolution ceased and filtered, washing with additional water. The solid collected was dried to provide the title compound as a solid (contaminated by ca. 10% mole $PPh_3$).

EXAMPLE 1B

2-(4-(4,4,5,5-tetramethyl-1,3,2-dioxaborolan-2-yl)-1H-pyrazol-1-yl)ethanol 4-(4,4,5,5-tetramethyl-1,3,2-dioxaborolan-2-yl)-1H-pyrazole (9.66 g, 49.8 mmol), 1,3-dioxolan-2-one (21 g, 238 mmol) and cesium carbonate (16 g, 49.1 mmol) were combined in a 100 mL round bottom flask. The reaction was warmed from room temperature to 100° C. in an oil bath, by which time the carbonate had melted and served as the solvent for the reaction, which remained a slurry. After heating for 3.5 hours, the reaction was cooled to room temperature and diluted with ethyl acetate, then filtered through Celite washing repeatedly with ethyl acetate. The filtrate was concentrated, then purified by chromatography on an Analogix® Intelliflash™ purification system using a SF60-200 g column at a flow rate of 80 mL/min, eluting as follows: 5 minutes at 20% ethyl acetate/hexanes, then ramped from 40% to 90% ethyl acetate/hexanes over 35 minutes, then 100% ethyl acetate for another 20 minutes, to provide the title compound.

EXAMPLE 1C

2-(4-(4-amino-3-(4-aminophenyl)thieno[3,2-c]pyridin-7-yl)-1H-pyrazol-1-yl)ethanol EXAMPLE 1A (6 g, 16.34 mmol), EXAMPLE 1B (4.8 g, 20.16 mmol), $PdCl_2(dppf)$ (1.2 g, 1.640 mmol) and sodium carbonate (4.6 g, 43.4 mmol) were combined in tetrahydrofuran (400 mL), methanol (80 mL) and water (80 mL), and the reaction was degassed by bubbling $N_2$ through the mixture for 1 hour. The reaction was then heated to 80° C. for 2 hours, then allowed to cool and diluted with 300 mL ethyl acetate. The mixture was partitioned with $H_2O$ (500 mL) and the aqueous layer was extracted with ethyl acetate (2×300 mL). The combined organic extracts were washed with brine, dried

EXAMPLE 1D

N-(4-{4-amino-7-[1-(2-hydroxyethyl)-1H-pyrazol-4-yl]thieno[3,2-c]pyridin-3-yl}phenyl)-N'-(3-fluorophenyl)urea EXAMPLE 1C (2 g, 5.69 mmol) was dissolved in N,N-dimethylformamide (80 ml) and the flask was chilled in a −20° C. bath. 1-fluoro-3-isocyanatobenzene (0.715 ml, 6.26 mmol) was added dropwise and the reaction was allowed to warm slowly to room temperature and stirred overnight. The reaction was diluted with water (500 mL) and ethyl acetate (75 mL) and stirred to digest for 1 hour. The mixture was then placed in a separatory funnel. After the layers were allowed to separate, the lower aqueous layer was drained off. Near the interface of the two layers there was a significant amount of precipitate. That material and the organic layer were filtered, giving a solid. The solid was rinsed with ethyl acetate and dried to give the title compound. $^1$H NMR (300 MHz, DMSO-$d_6$) δ ppm 3.80 (q, J=5.65 Hz, 2H) 4.23 (t, J=5.59 Hz, 2H) 4.96 (t, J=5.09 Hz, 1H) 5.42 (s, 2H) 6.80 (td, J=8.31, 2.37 Hz, 1H) 7.15 (dd, J=8.14, 1.02 Hz, 1H) 7.32 (td, J=8.22, 6.95 Hz, 1H) 7.41 (d, J=8.81 Hz, 2H) 7.51 (ddd, J=11.70, 2.37, 2.20 Hz, 1H) 7.50 (s, 1H) 7.61 (d, J=8.81 Hz, 2H) 7.91 (d, J=1.02 Hz, 1H) 8.05 (s, 1H) 8.15 (d, J=0.68 Hz, 1H) 8.96 (s, 1H) 8.99 (s, 1H); MS (ESI(+)) m/z 489.1 (M+H)+.

EXAMPLE 2

N-(4-{4-amino-7-[1-(2-hydroxyethyl)-1H-pyrazol-4-yl]thieno[3,2-c]pyridin-3-yl}phenyl)-N'-[4-(difluoromethoxy)phenyl]urea The title compound was prepared by substituting 1-(difluoromethoxy)-4-isocyanatobenzene for 1-fluoro-3-isocyanatobenzene in EXAMPLE 1D. $^1$H NMR (300 MHz, DMSO-$d_6$) δ ppm 3.80 (q, J=5.4 Hz, 2H) 4.23 (t, J=5.6 Hz, 2H) 4.95 (t, J=5.4 Hz, 1 H) 5.41 (br s, 2H) 7.13 (t, J=74.4 Hz, 1H) 7.13 (d, J=8.8 Hz, 2H) 7.39 (d, J=8.5 Hz, 2H) 7.48-7.55 (m, 3H) 7.61 (d, J=8.5 Hz, 2H) 7.90 (s, 1H) 8.05 (s, 1H) 8.15 (s, 1H) 8.85 (s, 1 H) 8.91 (s, 1H); MS (ESI(+)) m/e 537 (M+H)+.

EXAMPLE 3

N-[4-(4-amino-7-{1-[(2S)-2-hydroxypropyl]-1H-pyrazol-4-yl}thieno[3,2-c]pyridin-3-yl)phenyl]-N'-(3-methylphenyl)urea The title compound was prepared following the procedures of EXAMPLES 1B-1D except substituting (S)-4-methyl-1,3-dioxolan-2-one for 1,3-dioxolan-2-one and 1-isocyanato-3-methylbenzene for 1-fluoro-3-isocyanatobenzene in EXAMPLES 1B and 1D, respectively. $^1$H NMR (300 MHz, DMSO-$d_6$) δ ppm 1.09 (d, J=6.10 Hz, 3H) 2.29 (s, 3H) 4.01- 4.12 (m, 3H) 4.96 (d, J=4.75 Hz, 1H) 5.43 (s, 2H) 6.81 (d, J=7.46 Hz, 1H) 7.17 (t, J=7.80 Hz, 1H) 7.26 (app d, J=9.15 Hz, 1H) 7.32 (s, 1H) 7.39 (d, J=8.48 Hz, 2H) 7.50 (s, 1 H) 7.61 (d, J=8.81 Hz, 2H) 7.90 (d, J=0.68 Hz, 1H) 8.05 (s, 1H) 8.13 (d, J=1.02 Hz, 1H) 8.66 (s, 1H) 8.86 (s, 1H); MS (ESI(+)) m/z 499.2 (M+H)+.

EXAMPLE 4

N-(4-{4-amino-7-[1-(2-hydroxy-2-methylpropyl)-1H-pyrazol-4-yl]thieno[3,2-c]pyridin-3-yl}phenyl)-N'-(4-methoxyphenyl)urea

EXAMPLE 4A 2-methyl-1-(4-(4,4,5,5-tetramethyl-1,3,2-dioxaborolan-2-yl)-1H-pyrazol-1-yl)propan-2-ol A mixture of 4-(4,4,5,5-tetramethyl-1,3,2-dioxaborolan-2-yl)-1H-pyrazole (500 mg, 2.57 mmol), $Cs_2CO_3$ (840 mg, 2.57 mmol) and 2,2-dimethyloxirane (2 mL) was heated in a sealed vial at 120° C. for 3 minutes with stirring in a Smith Synthesizer microwave oven (at 300 W), then allowed to cool and diluted with $CH_2Cl_2$. The resulting suspension was filtered, and the filtrate was concentrated to give the title compound.

EXAMPLE 4B

N-(4-{4-amino-7-[1-(2-hydroxy-2-methylpropyl)-1H-pyrazol-4-yl]thieno[3,2-c]pyridin-3-yl}phenyl)-N'-(4-methoxyphenyl)urea The title compound was prepared following the procedures of EXAMPLES 1C-1D except substituting EXAMPLE 4A for EXAMPLE 1B and 1-isocyanato-4-methoxybenzene for 1-fluoro-3-isocyanatobenzene in EXAMPLES 1C and EXAMPLE 1D, respectively. $^1$H NMR (300 MHz, DMSO-$d_6$) δ ppm 1.12 (s, 6H) 3.72 (s, 3H) 4.11 (s, 2H) 4.76 (s, 1H) 5.43 (s, 2H) 6.88 (d, J=9.15 Hz, 2H) 7.38 (d, J=8.81 Hz, 4H) 7.49 (s, 1H) 7.60 (d, J=8.81 Hz, 2 H) 7.89 (d, J=0.68 Hz, 1H) 8.06 (s, 1H) 8.11 (d, J=0.68 Hz, 1H) 8.55 (s, 1H) 8.80 (s, 1H); MS (ESI(+)) m/z 529.3 (M+H)+.

EXAMPLE 5

N-[4-(4-amino-7-{1-[(2S)-2,3-dihydroxypropyl]-1H-pyrazol-4-yl}thieno[3,2-c]pyridin-3-yl)phenyl]-N'-(4-methoxyphenyl)urea

EXAMPLE 5A (S)-1-((2,2-dimethyl-1,3-dioxolan-4-yl)methyl)-4-(4,4,5,5-tetramethyl-1,3,2-dioxaborolan-2-yl)-1H-pyrazole A mixture of (R)-(2,2-dimethyl-1,3-dioxolan-4-yl)methyl methanesulfonate (1.08, 5.15 mmol), 4-(4,4,5,5-tetramethyl-1,3,2-dioxaborolan-2-yl)-1H-pyrazole (1 g, 5.15 mmol) and NaH (262 mg, 10.9 mmol) in N,N-dimethylformamide (25 mL) was heated at 90° C. for 3 hours, then allowed to cool to room temperature., quenched with water and extracted with ethyl acetate (3×). The combined organics were washed with brine, concentrated and the residue was purified by chromatography on an Analogix® Intelliflash™ purification system using a SF25-25 g column at a flow rate of 80 mL/minute, eluting with 0% to 30% ethyl acetate:hexanes over 30 minutes to give the title compound.

EXAMPLE 5B (S)-1-(4-(4-amino-7-(1-((2,2-dimethyl-1,3-dioxolan-4-yl)methyl)-1H-pyrazol-4-yl)thieno[3,2-c]pyridin-3-yl)phenyl)-3-(4-methoxyphenyl)urea The title compound was prepared following the procedures of EXAMPLES 1C-1D except substituting EXAMPLE 5A for 1B and 1-isocyanato-4-methoxybenzene for 1-fluoro-3-isocyanatobenzene in EXAMPLES 1B and 1D, respectively.

EXAMPLE 5C

N-[4-(4-amino-7-{1-[(2S)-2,3-dihydroxypropyl]-1H-pyrazol-4-yl}thieno[3,2-c]pyridin-3-yl)phenyl]-N'-(4-methoxyphenyl)urea A solution of EXAMPLE 5B (44 mg, 0.077 mL) in tetrahydrofuran (2 mL) was treated with 2N HCl (1 mL), then stirred at room temperature for 18 hours. The resulting suspension was filtered and the solid was collected and dried to give the title compound. $^1$H NMR (300 MHz, DMSO-$d_6$) δ ppm 3.72 (s, 3H) 3.32-3.45 (m, 4H) 3.84-3.91 (m, 1H) 4.12 (dd, J=13.90, 7.80 Hz, 1H) 4.34 (dd, J=13.90, 3.73 Hz, 1H) 6.89 (d, J=9.15 Hz, 2H) 6.89-6.93 (m, 2H) 7.38 (d, J=9.15 Hz, 2H) 7.45 (d, J=8.81 Hz, 2H) 7.65 (d, J=8.81 Hz, 2H) 7.94 (s, 1H) 7.99 (d, J=0.68 Hz, 1H) 8.06 (s, 1H) 8.28 (d, J=0.68 Hz, 1H) 8.72 (s, 1H) 9.05 (s, 1H); MS (ESI(+)) m/z 531.2 (M+H)$^+$.

EXAMPLE 6

N-{4-[4-amino-7-(1H-pyrazol-4-yl)thieno[3,2-c]pyridin-3-yl]phenyl}-N'-(3-methylphenyl)urea Example 6 is described as EXAMPLE 703 in WO 2005/10009.

The foregoing is meant to illustrate the invention but not to limit it. Variations and changes obvious to one skilled in the art are intended to be within the scope of the invention as defined in the claims.

We claim:
1. A compound having Formula I

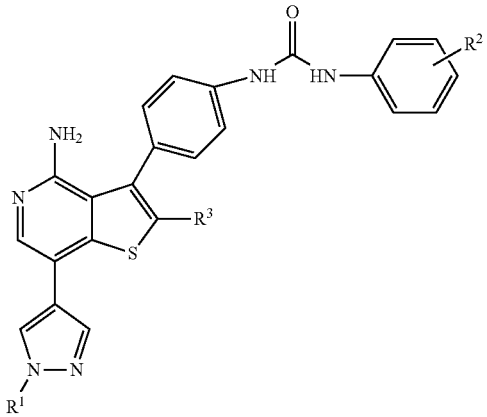

or a therapeutically acceptable salt thereof,
wherein
R$^1$ is hydroxyalkyl;
R$^2$ is selected from the group consisting of alkoxy, alkyl, halo, and haloalkoxy; and
R$^3$ is hydrogen or alkyl.

2. A compound which is N-(4-{4-amino-7-[1-(2-hydroxyethyl)-1H-pyrazol-4-yl]thieno[3,2-c]pyridin-3-yl}phenyl)-N'-(3-fluorophenyl)urea; or a therapeutically acceptable salt thereof.

3. A compound which is N-(4-{4-amino-7-[1-(2-hydroxyethyl)-1H-pyrazol-4-yl]thieno[3,2-c]pyridin-3-yl}phenyl)-N'-[4-(difluoromethoxy)phenyl]urea; or a therapeutically acceptable salt thereof.

4. A compound which is N-[4-(4-amino-7-{1-[(2S)-2-hydroxypropyl]-1H-pyrazol-4-yl}thieno[3,2-c]pyridin-3-yl)phenyl]-N'-(3-methylphenyl)urea; or a therapeutically acceptable salt thereof.

5. A compound which is N-(4-{4-amino-7-[1-(2-hydroxy-2-methylpropyl)-1H-pyrazol-4-yl]thieno[3,2-c]pyridin-3-yl}phenyl)-N-(4-methoxyphenyl)urea; or a therapeutically acceptable salt thereof.

6. A compound which is N-[4-(4-amino-7-{1-[(2S)-2,3-dihydroxypropyl]-1H-pyrazol-4-yl}thieno[3,2-c]pyridin-3-yl)phenyl]-N-(4-methoxyphenyl)urea; or a therapeutically acceptable salt thereof.

7. A composition comprising an excipient and a therapeutically effective amount of a compound of claim 1, or a therapeutically acceptable salt thereof.

* * * * *

UNITED STATES PATENT AND TRADEMARK OFFICE
CERTIFICATE OF CORRECTION

PATENT NO. : 8,722,890 B2  
APPLICATION NO. : 13/585333  
DATED : May 13, 2014  
INVENTOR(S) : Michaelides et al.

Page 1 of 1

It is certified that error appears in the above-identified patent and that said Letters Patent is hereby corrected as shown below:

In the Claims

Column 32, line 41, claim 5: "-N-" to read as -- -N'- --

Column 32, line 45, claim 6: "-N-" to read as -- -N'- --

Signed and Sealed this
Seventeenth Day of February, 2015

Michelle K. Lee
*Deputy Director of the United States Patent and Trademark Office*